(12) United States Patent
Faleris et al.

(10) Patent No.: US 10,342,562 B2
(45) Date of Patent: Jul. 9, 2019

(54) CAPTURE-TOOL FOR MANIPULATING AND ENTUBULATING NERVES

(71) Applicant: AxoGen Corporation, Alachua, FL (US)

(72) Inventors: Jennifer Faleris, Alachua, FL (US); Anne Engemann, Alachua, FL (US); Curt Deister, Alachua, FL (US)

(73) Assignee: AxoGen Corporation, Alachua, FL (US)

( * ) Notice: Subject to any disclaimer, the term of this patent is extended or adjusted under 35 U.S.C. 154(b) by 109 days.

(21) Appl. No.: 15/416,290

(22) Filed: Jan. 26, 2017

(65) Prior Publication Data

US 2018/0206871 A1     Jul. 26, 2018

(51) Int. Cl.
*A61B 17/30*     (2006.01)
*A61B 17/11*     (2006.01)

(52) U.S. Cl.
CPC ........... *A61B 17/30* (2013.01); *A61B 17/1128* (2013.01); *A61B 2017/308* (2013.01)

(58) Field of Classification Search
CPC ............... A61B 17/1128; A61B 17/11; A61B 2017/306; A61B 2017/308
See application file for complete search history.

(56) References Cited

U.S. PATENT DOCUMENTS

| | | | |
|---|---|---|---|
| 6,210,323 B1 | 4/2001 | Gilhuly et al. | |
| 6,241,658 B1 | 6/2001 | Goodrich | |
| 6,656,109 B2 * | 12/2003 | DeVries | A61B 17/02 128/897 |
| 2001/0025161 A1 | 9/2001 | Martinez | |
| 2004/0186488 A1 * | 9/2004 | Droese | A61B 17/1128 606/152 |
| 2005/0107671 A1 * | 5/2005 | McKinley | A61B 17/025 600/235 |

OTHER PUBLICATIONS

Isaacs, J. et al., "Technical Assessment of Connector-Assisted Nerve Repair," *Journal of Hand Surg Am.*, Jul. 2016, pp. 760-766, vol. 41, No. 7.
International Search Report issued in counterpart International Application Serial No. PCT/US2018/015464 dated May 8, 2018.

* cited by examiner

*Primary Examiner* — Carrie R Dorna
(74) *Attorney, Agent, or Firm* — Heath M. Sargeant; Holland & Knight LLP (57) ABSTRACT

A capture-tool for manipulation of tissue utilizes vacuum to hold the tissue in place. An extension attached to a vacuum source at one end and a vacuum arm at another end creates a vacuum force through the extension and vacuum arm. The vacuum arm has a support surface with ports therein at which low pressure areas are formed by the vacuum force. The low pressure areas draw tissue against the supporting surface to hold it in place, as long as the vacuum force is active.

20 Claims, 6 Drawing Sheets

CAPTURE-TOOL FOR MANIPULATING AND ENTUBULATING NERVES

This invention was made with government support under grant no. W81XWH-13-1-0448 awarded by the U.S. Department of Defense through the office of U.S. Army Medical Command. The government has certain rights in the invention.

BACKGROUND OF INVENTION

Manipulation of tissue for surgical repair can be challenging. Nerve tissue is particularly susceptible to damage and care must be taken to handle only the thin outer epineurium to avoid trauma to the internal fascicles. Improper handling can result in poor functional outcomes, extended healing times, pain, neuromas, or other undesirable side-effects.

Standard surgical instruments often utilized for manipulation require grasping or pinching a nerve to place it in position for entubulation or other repairs.

It has been shown that with current procedures and instruments 13 of 15 connector-only nerve repairs performed by inexperienced surgeons are judged to be fair or poor. (Isaacs, J., Journal of Hand Surg Am. 2016 July; 41(7):760-6). While these numbers can be attributed somewhat to the skill of the surgeon, there is clearly a need for a surgical instrument that can capture and manipulate delicate nerve tissue that does not require pinching or other application of force to the tissue, which can contribute to the inferior quality of a repair.

BRIEF SUMMARY

In accordance with the subject invention, the problem of holding or capturing nerve tissue without pinching, and without the application of other direct or concentrated force to the tissue, which can crush internal structures, is solved by the use of a vacuum capture-tool for suctioning nerve tissue against the instrument.

The capture-tool can have a supporting surface with one or more ports. The capture-tool can be connected to a pump or other device that can create low-pressure or vacuum force at the ports. Placing the ports against a nerve allows the low pressure at the ports to pull or suction the outside of the nerve, or the epineurium, against the ports, where it can be held in place against, and supported by, the supporting surface of the capture-tool. Embodiments of the subject invention can be used to suck in air or other gases, as well as liquids or fluids. Thus, the low pressure at the ports is not limited to pulling or suctioning only air or gas.

The epineurium is a dense connective tissue surrounding most nerve tissues. Advantageously, gentle negative pressure applied to the epineurium has minimal or no effect on the other internal tissues of a nerve, if the vacuum force is properly adjusted.

In certain embodiments, the capture-tool is configured as a hand-piece for direct manual manipulation. Alternatively, the capture-tool can be configured as an extension of a robotic arm or other actuation device for indirect or automated manipulation.

Whether configured for manual or robotic manipulation, the capture-tool can be directly or indirectly operably attachable to a vacuum source. In further embodiments, the capture-tool is directly or indirectly operably attached to an air source that expels or blows air or gas. The vacuum source and the air source can be the same device or apparatus.

The working end of the capture-tool can have a vacuum arm with one or more ports through which the vacuum source can create low pressure areas. The ports can be arranged on the supporting surface, so that they can hold a nerve tissue linearly or longitudinally to the vacuum arm and/or a branch thereof for easier coaptation or entubulation. The vacuum arm can also be angled to facilitate manipulation of the tool against a nerve end for easier and more accurate manipulation of the suctioned nerve. A vacuum atm can range in size to appropriately cradle tissue of different widths and lengths. A vacuum arm can further be an elongated, linear shape or a non-linear shape, such that it has bifurcations, extensions or branches.

The vacuum through the capture-tool can be adjusted to provide the necessary low pressure at the ports to maintain the position of the nerve against the supporting surface, preferably without actually drawing tissue, or a significant amount of tissue, into the ports. The vacuum can also be adjusted during a procedure to increase or decrease the vacuum force by which the tissue is held against the ports and supporting surface. Alternatively, a control mechanism 8 can be used to turn the vacuum off and/or reverse it, so that air or gas can be expelled from the ports. This can facilitate release of tissue from the vacuum arm supporting surface, should the tissue not release automatically when the vacuum is turned off. The size or diameter of ports and the number of ports can also vary. In certain embodiments, the ports have beveled, rounded, or blunt edges to inhibit cutting or fraying of the nerve where it meets with the ports.

The capture-tool of the subject invention successfully addresses disadvantages associated with previously known devices and methods, and provides certain attributes and advantages, which have not been realized by these known devices. The subject invention provides novel capture-tools capable of holding or securing a nerve safely and securely with minimal or no damage to the interior or exterior of tissue. The shape and configuration of the capture-tool and components thereof make it well-suited for manipulation of nerve tissue.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention.

FIGS. 7A, 7B, and 7C illustrate embodiments of non-linear vacuum arms, according to the subject invention.

FIGS. 13A, 13B, and 13C illustrate alternative embodiments of an internal conduit in a vacuum arm.

DETAILED DISCLOSURE

The subject invention provides devices and methods for manipulating tissue without pinching or applying direct compressive force to tissues. More specifically, the subject invention provides a capture-tool, or similarly-operating device, for use in suctioning a tissue against a surface. The surface can act to support the tissue while it is being suctioned. When the vacuum force is turned off, the low pressure in the ports decreases or ceases and the tissue can be released from the surface. A positive pressure expelled through the ports can also be used to aid the release of tissue from the surface.

The subject invention is particularly useful in the field of surgical nerve repair and procedures, in particular repairs and procedures to place tissue, such as nerve tissue, in a particular position for repair or for entubulation, such as within an implant. The subject invention is especially useful where precise, delicate maneuvers are required with soft tissues.

While the subject application describes, and many of the terms herein relate to, a use for nerve repair and treatment, other modifications and uses, such as repairs to vessels, tendons, muscles, and fascia, will be apparent to a person with skill in the art and having benefit of the subject disclosure. Such modification and alternative uses are contemplated to be within the scope of the present invention.

In the description that follows, a number of terms are used in relation to the invention and nerves and nerve repair and treatment. In order to provide a clear and consistent understanding of the specification and claims, including the scope to be given such terms, the following definitions are provided.

The terms "tissue" and "nerve" are used interchangeably herein and are merely for literary convenience. The embodiments of the subject invention could be utilized with any animal or human tissue in need of being held in place or manipulated, particularly for surgical procedures.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct or indirect, physical or remote.

The figures and descriptions of embodiments of the present invention have, in some instances, been simplified to illustrate elements that are relevant for a clear understanding of the invention, while eliminating, for purposes of clarity, other elements that may be well known.

Finally, reference is made throughout the application to the "proximal end" and the "distal end." As used herein, the proximal end is that end located nearest to the user when in use or the end positioned furthest from a patient during use. Conversely, the distal end of the capture-tool is that end placed closest to or in contact with a patient or a tissue.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached Figures on which the same reference numerals are used throughout to indicate the same or similar components. With reference to the attached Figures, it can be seen that the capture-tool 10 of the subject invention can comprise a handle 20 at or near the proximal end 2 by which the capture-tool can be held by a user, an extension 50 leading from the handle and having a channel 55 through which a vacuum source 6 can move air or other gases away from or towards a vacuum arm 100 with a supporting surface 110 and one or more ports 150 therein, so as to create low pressure areas along the supporting surface or to expel air or gasses. A control mechanism 8 can be used to adjust or change the flow of air depending on whether vacuum or expelled air is required.

Figures 1, 2, 3, 12:
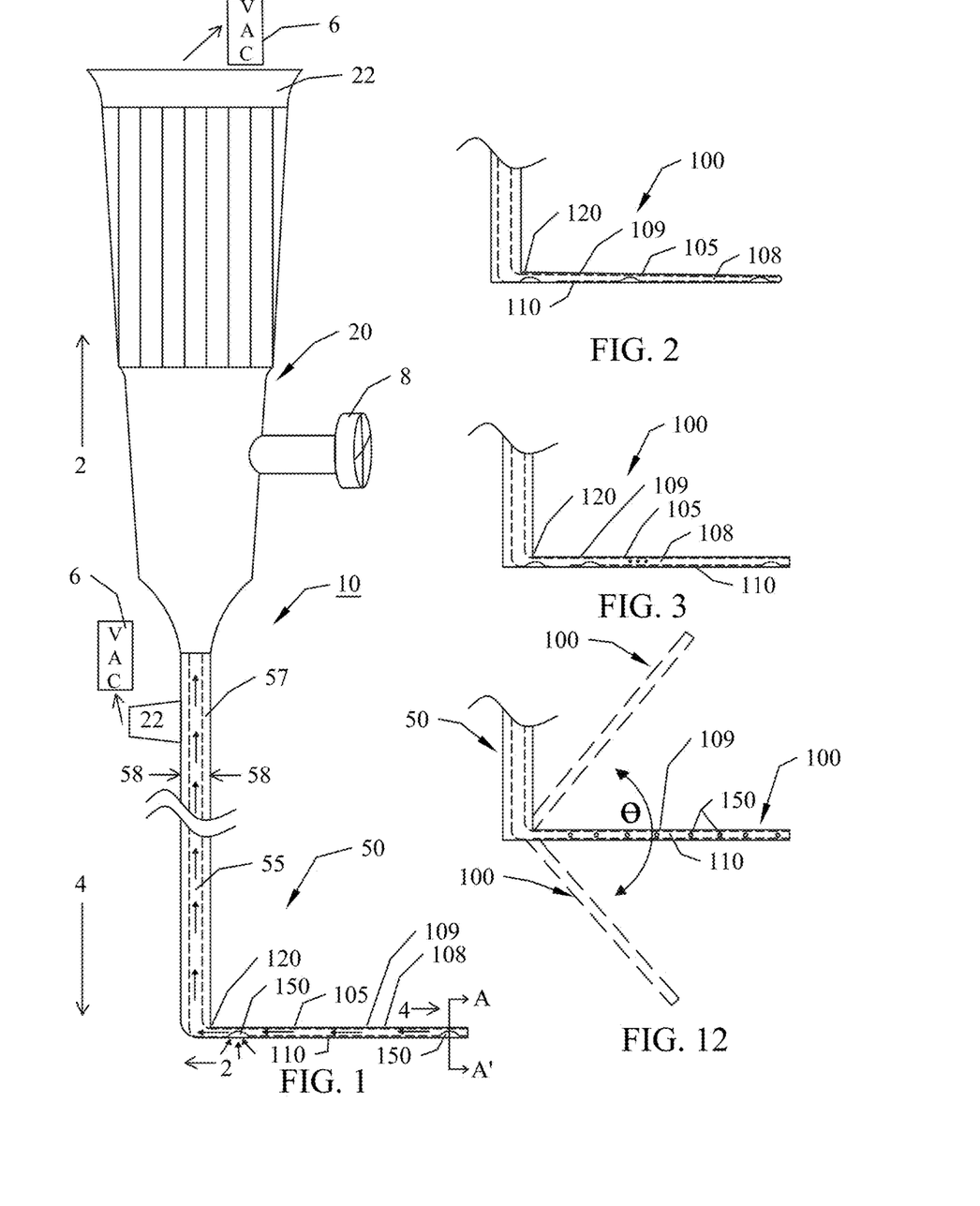
FIG. 1 is an illustration of one embodiment of a capture-tool, according to the subject invention. The embodiment shown has two ports at either end of the supporting surface.
FIG. 2 is an illustration of an embodiment of a vacuum arm for a capture-tool, according to the subject invention. The embodiment shown has three ports arranged along the supporting surface.
FIG. 3 is an illustration of another embodiment of a vacuum arm for a capture-tool, according to the subject invention. The embodiment shown can have multiple ports, indicated by the ellipses, arranged along the supporting surface.
FIG. 12 illustrates an alternative embodiment of a capture-tool, according to the subject invention, where the ports are located on a side surface. Also illustrated are alternative angles for the vacuum atm, relative to the extension.

With regard to the handle 20, there can be any number of configurations employed to hold and manipulate the capture-tool 10. As such, the subject invention is not limited to any particular style, ergonomics, or design for a handle. FIG. 1 illustrates one non-limiting example of a handle. The ability to determine the appropriate design and materials for a handle to be used for the capture-tool 10 of the subject invention is within the capability of one of ordinary skill in the art.

In one embodiment, the handle has a connector 22 for attachment to a vacuum source. Surgical suites or operating rooms often have a vacuum source for suctioning fluids and other materials away from a surgical site during surgical procedures. A connector 22 could be attachable to the same type of vacuum source 6. Alternatively, a separate or different vacuum source could be utilized. A person with skill in the art will be able to determine the most appropriate connector and vacuum source for use with capture-tool 10 embodiments of the subject invention.

Figure 8:
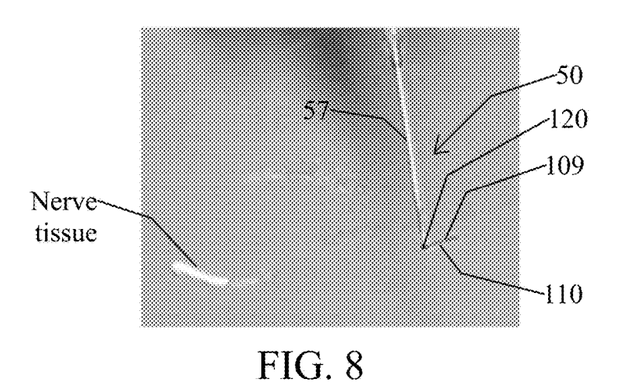
FIG. 8 is a photograph showing one embodiment of a capture-tool (right side), according to the subject invention. The left side of the photograph shows a section of nerve tissue.

The distal end 4 of the handle can have an extension 50 leading therefrom for directing the vacuum through the capture-tool. In one embodiment, the extension is a tubular structure having a wall 57 that defines at least one channel 55 longitudinal with the extension, where the proximal end 2 of the channel is attached to the vacuum source 6. In one embodiment, the extension is a rigid, tubular structure. In another embodiment, the extension is a flexible, semi-flexible, or otherwise bendable tubular structure. In a further embodiment, an extension can be some combination of both a rigid structure and a bendable structure. FIGS. 1 and 8 illustrate a non-limiting example of an extension attached to a handle.

There are numerous devices and methods that can be used to operably connect the channel in the extension to a vacuum source 6 or to an air source 9. Any configuration of an extension capable of directing vacuum or expelling air from an air source can be suitable as an extension for the subject invention.

In an alternative embodiment, the extension can be attached to the vacuum source 6 or air source 9 without utilization of a handle. There can be a vacuum connector 22 on the extension that connects directly to the vacuum source, one example of which is also shown in FIG. 1. The extension could also connect to the vacuum source without benefit of a connector, which is not shown in the Figures, but which would be understood by a person skilled in the art. With these embodiments, a handle would not be required, but could still be utilized if desired.

The dimensions of an extension can vary depending upon a variety of factors, including, but not limited to, the type of tissue with which it will be used, the amount of vacuum available for creating the necessary low pressure in the ports, the amount of pressure that can be exerted on the wall 57 of the extension, the number of ports 150 in the vacuum arm 100, and other factors known to those with skill in the art.

In one embodiment, the length of an extension is between approximately 10 cm and approximately 30 cm. In another embodiment, the length of an extension is between approximately 15 cm and approximately 24 cm. In a more specific embodiment, the length of an extension is between approximately 18 cm and approximately 20 cm.

Likewise, there can be a range of external diameters for an extension 50. The external diameter can also depend upon a variety of factors, including, but not limited to, the material utilized for the extension, the amount of vacuum force to be drawn through the one or more channels 55, the thickness of the wall 57, whether the extension is tapered, and other factors known to those with skill in the art.

In one embodiment, the extension has a consistent or substantially consistent diameter along the entire length. In a further embodiment, the external diameter 58 of an extension ranges between approximately 0.5 mm and approximately 10 mm. In another embodiment, the external diameter of an extension ranges between approximately 1 mm and approximately 7 mm. In a particular embodiment, the external diameter ranges between approximately 2 mm and approximately 5 mm.

In an alternative embodiment, the extension can also taper from the proximal end 2 to the distal end 4, such that the external diameter of the proximal end is larger than the external diameter at the distal end. This can facilitate attachment to a vacuum arm. With this embodiment, the external diameter can taper between any of the external diameter ranges mentioned above.

The diameter of the channel within the extension can depend upon the external diameter, the thickness of the wall material, the vacuum force that will be drawn through the channel, the material of the extension and other factors known to those with skill the art. It is within the skill of a person trained in the art to determine the appropriate diameter or diameters for a channel. Such variations are within the scope of this invention.

Figure 6A:
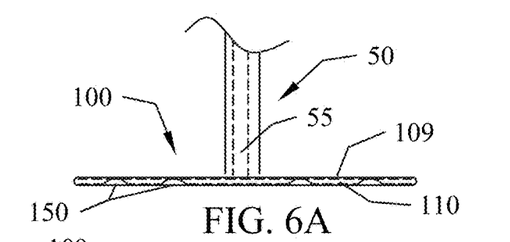
FIGS. 6A and 6B are a side elevation view and a top end view, respectively, of an alternative embodiment of an extension and vacuum arm, according to the subject invention.
Figure 6B:
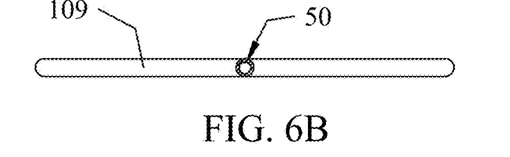

A capture-tool can have a vacuum arm 100 extending from the distal end 4 of the extension 50. The vacuum arm can attach to the distal end of the extension. In one embodiment, the vacuum arm attaches to the distal end 4 of the extension at a connection point 120, which is shown, for example, in FIGS. 1-3 and 8. The connection point can be anywhere along the length of the vacuum arm. FIGS. 1-3 and 8 illustrate a non-limiting example of an extension attached at a connection point at one end of the vacuum arm. FIGS. 6A and 6B illustrate another non-limiting example of an extension attached at a connection point nearer the center of the vacuum arm. FIG. 6A is a side view of an extension and a vacuum arm and FIG. 6B is a proximal end view of FIG. 6A. An extension can also be attached at a connection point at other locations on the vacuum arm. It is within the skill of a person trained in the art to determine a location for a connection point on a vacuum arm. Such variations are within the scope of this invention.

Figure 7A:
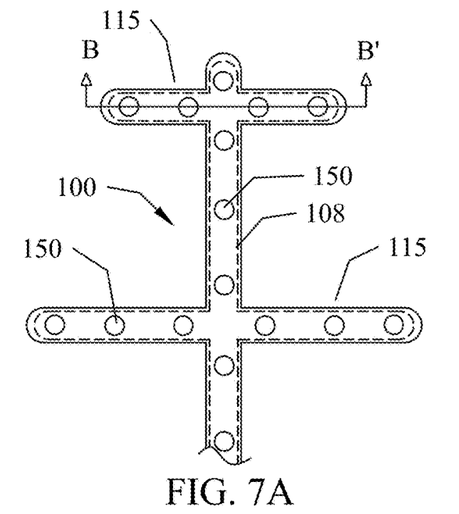
Figure 7B:
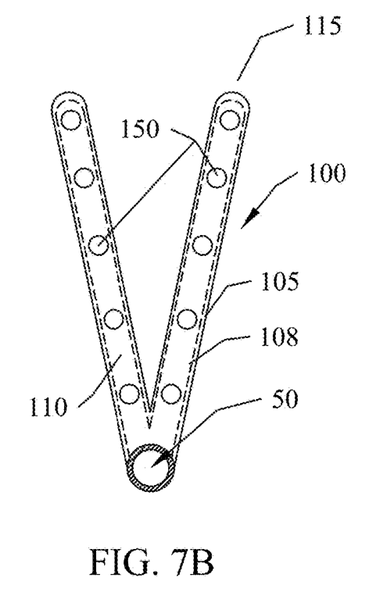

In one embodiment, a vacuum arm 100 has an elongated, linear form, such as shown, for example, in FIGS. 3, 5A-5C, 6A, and 8. With this embodiment, a connection point 120 for the extension can be anywhere along the length of the vacuum arm. In an alternative embodiment, a vacuum arm is not an elongated liner form. A vacuum arm can have extensions, bifurcations, splits, forks, or other types of branches 115. FIG. 7A illustrates a non-limiting example of a vacuum arm with perpendicular extensions. FIG. 7B illustrates a non-limiting example of a vacuum arm that is forked. As with a linear, elongated vacuum arm, a branch 115 can be attached at a connection point anywhere on a non-linear or extended vacuum arm.

Figures 13A, 13B, 13C:
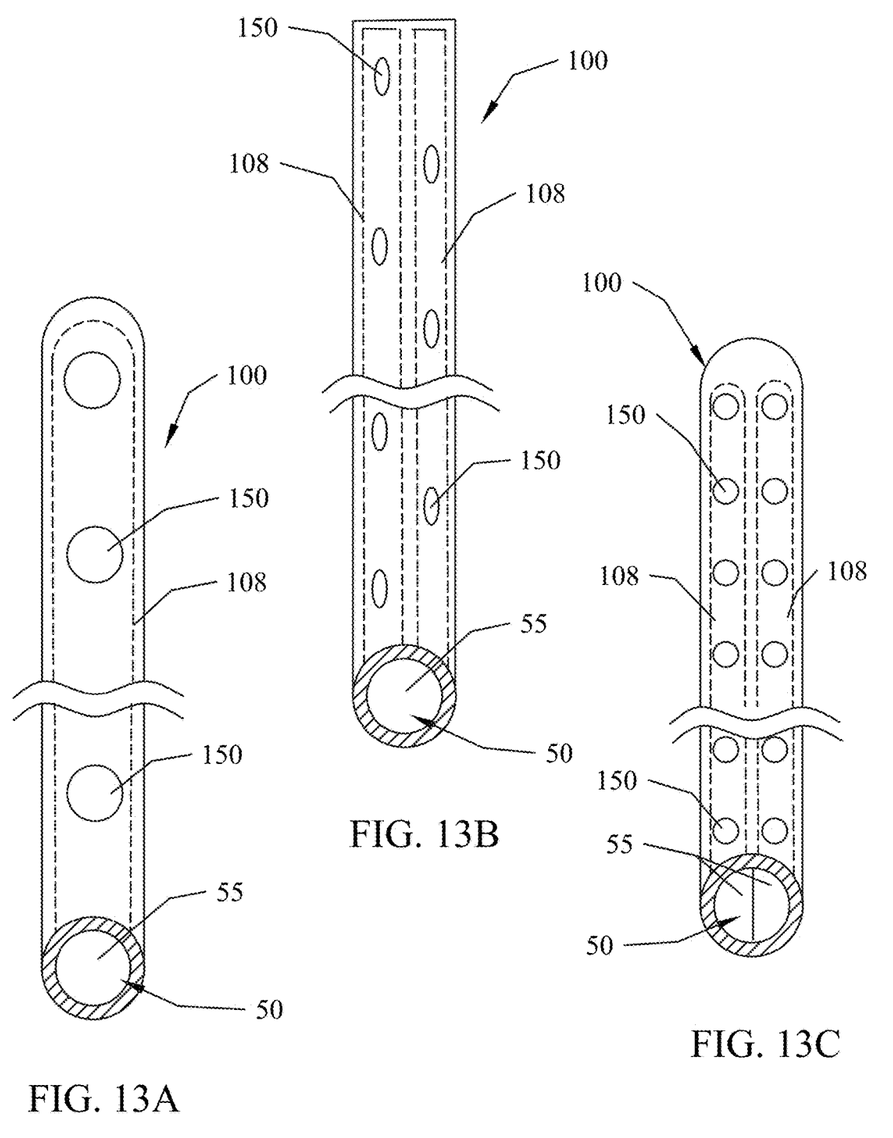
FIG. 13A shows a single conduit leading into a channel in the extension.
FIG. 13B shows dual internal conduits leading into a channel in an extension.
FIG. 13C shows dual internal conduits leading into two separate channels in an extension.

In one embodiment, the vacuum arm is a tubular structure having an external sleeve 105 that defines an internal conduit 108. In one embodiment, the internal conduit in the vacuum arm is continuous or integral with the channel 55 in the extension. This can direct the flow of expelled air and/or the vacuum force through ports into the conduit and further into the channel, as indicated by the arrows at the ports 150, in the channel 55 and in the internal conduit 108 in FIG. 1. In one embodiment, there is a single internal conduit that is continuous or integral with one channel 55, such that there is one current of vacuum or expelled air. One example of this is shown in FIG. 13A. In another embodiment, there are two or more internal conduits continuous or integral with one channel, such that there are multiple currents of vacuum and/or expelled air leading to, or from, one channel. An example of this is shown in FIG. 13B. In yet another embodiment, there are two or more internal conduits 108, where each is continuous or integral with a different channel 55, such that each internal conduit and channel form separate currents of vacuum and expelled air. FIG. 13C shows a non-limiting example of this embodiment. The more independent the currents of vacuum and expelled air, the more can control there can be over the amount of pressure in the ports 150. Each independent current could also be different, where one current is a vacuum while the other is expelling air.

A vacuum arm can be attached to the distal end of an extension at any angle that facilitates suction of a tissue. In one embodiment, a vacuum arm can be attached to an extension at any angle θ between approximately 30° and approximately 180° relative to the extension 50. FIGS. 1-3 and 6 illustrate embodiments where the vacuum arm extends substantially perpendicular to the extension. FIG. 12 illustrates embodiments, using dashed lines, where the vacuum arm extends from and is attached at different angles to the extension.

Figure 4A:
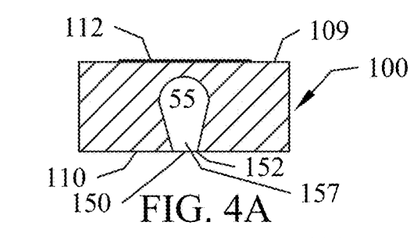
FIGS. 4A, 4B, 4C and 4D represent cross-sections taken along line A-A' in FIG. 1, to illustrate alternative circumferential shapes for a vacuum arm.
Figure 4B:
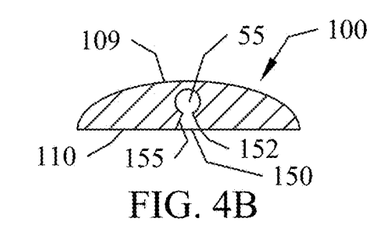
Figure 4C:
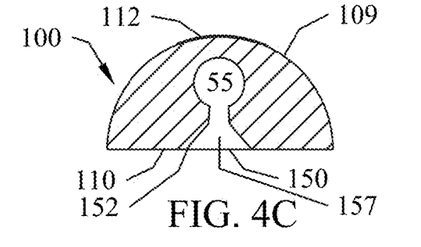
Figure 5A:
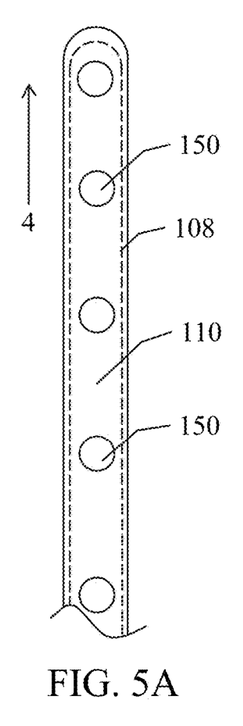
FIGS. 5A, 5B, and 5C are illustrations of alternative arrangements of the ports in a vacuum arm of a capture-tool, according to the subject invention.
Figure 5B:
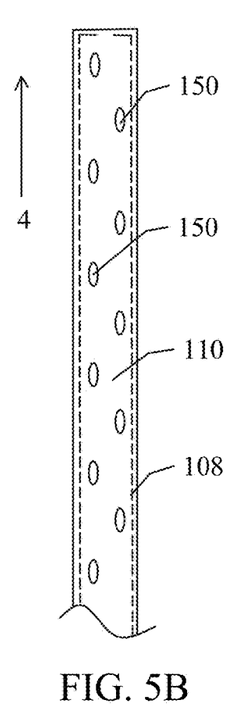
Figure 5C:
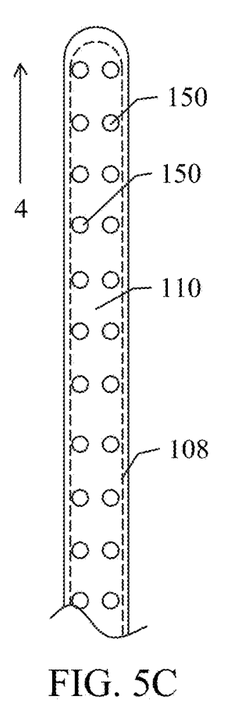

In one embodiment, the distal end 4 of a vacuum arm has a blunt finish or surface, such that there is a flat surface and/or squared or pointed corners. FIGS. 1, 3 and 5B illustrate examples where the distal end of the vacuum arm is squared-off or does not have rounded corners. In an alternative embodiment, the distal end of a vacuum arm is rounded, beveled, or otherwise finished to minimize corners and have a smooth surface. FIGS. 2, 5A, and 5C illustrate examples where the distal end is rounded or has minimal or no sharp corners. In still another embodiment, the distal end has a shape that is some combination of squared and rounded. FIG. 4C is a cross-section that illustrates an example of a vacuum arm with a flat supporting surface 100 having defined edges and a viewing surface that is rounded.

In one embodiment, a vacuum arm has a viewing surface 109 directed towards the proximal end of the extension 50 and a supporting surface 110, having ports therein, which can be located on any surface opposite to or adjacent to the viewing surface. The supporting surface can be used to contact the tissue to be suctioned by the ports and support the tissue. In one embodiment, the supporting surface is directly opposite to the viewing surface, as shown by the non-limiting examples in FIGS. 1-3, and 4A-4D. In an alternative embodiment, a supporting surface is located on a side adjacent to, or that is not directly opposite to, the viewing surface. FIG. 12 illustrates one example of a supporting surface 110 that is adjacent to the viewing surface 109.

Figure 10:
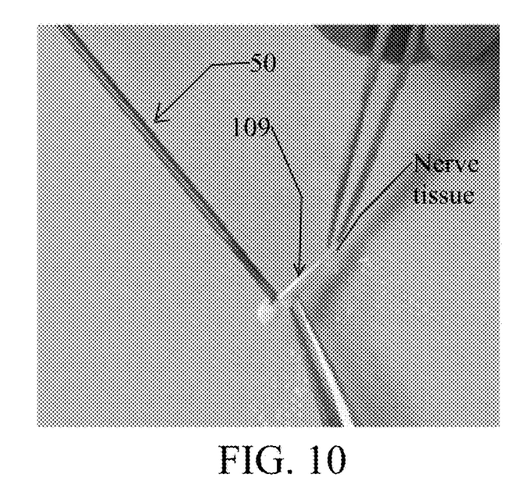
FIG. 10 is a photograph showing the suctioned nerve in FIG. 9 being manipulated with other instruments without the suctioned nerve being disconnected from the supporting surface.

The viewing surface can be used to orient the vacuum arm relative to a tissue. Preferably, all or most of the viewing surface can be seen when tissue is against the supporting surface. This can be advantageous when orienting the tissue for implantation, repair, or entubulation. In one embodiment, the material of the vacuum arm provides sufficient visibility to observe the viewing surface at all times. For example, FIG. 10 shows an example of a vacuum arm where the metallic material of the vacuum arm provides a natural reflective surface, which can be seen in the photograph. In another embodiment, the viewing surface can have an additional visibility component 112 that makes it easier to see the surface. FIGS. 4A and 4C illustrate examples having a visibility component on the viewing surface to improve visibility.

There are a variety of visibility components that could be used to improve observation of the viewing surface, including, but not limited to, high visibility paints or other coatings; luminescent paints or coatings or markers; reflective paints, coatings, or markers; special surface treatments, such as mirror finishes; and other methods or devices known to those with skill in the art.

Figure 9:
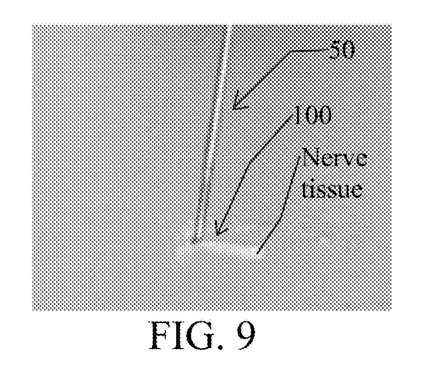
FIG. 9 is a photograph showing the capture-tool embodiment in FIG. 8, to which the section of nerve has been suctioned against the supporting surface of the vacuum arm.

The supporting surface 110 is the surface of the vacuum arm having one or more ports 150 against which a tissue can be sucked, as shown, by way of example, in FIG. 9. When the tissue is against the supporting surface it can be advantageous for the supporting surface to be free of protrusions, edges, nibs, scratches, hatching, or other surface features or defects that can fray, attach to, penetrate, or otherwise damage a tissue, particularly a nerve, placed thereagainst. It can also be advantageous for the surface to have a circumferential form that promotes support of a tissue thereagainst.

In one embodiment, the supporting surface 110 is flat, or substantially flat. This allows the supporting surface to be generally generic for use with a variety of types and sizes of tissues. FIGS. 4A, 4B, and 4C illustrate examples of flat, or substantially flat, supporting surfaces 110. In a further embodiment, the supporting surface could be slanted toward one or both sides of the viewing surface, in addition to being flat, or substantially flat. FIG. 4A illustrates one example of this embodiment, where one side is slanted upwards toward the viewing surface.

Figure 4D:
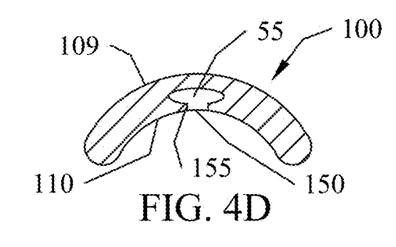
Figure 7C:
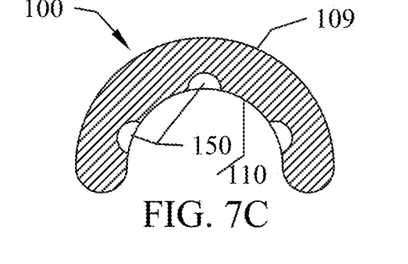
FIG. 7C illustrates a specific embodiment where a non-linear vacuum arm is curved along the supporting surface.

In specific situations, it can be advantageous for the supporting surface to be curved or form fitting for a tissue. By way of example, nerve tissue tends to have a naturally circular or rounded circumferential shape. Furthermore, nerve tissue can be very delicate, flexible, or even gelatinous in texture, making it difficult to manipulate. Suctioning such an amorphous tissue type against a flat surface can cause the tissue to flatten out as well, making it difficult to work with. In one embodiment, the supporting surface 110 is more rounded or curved to better accommodate the natural shape of such tissue and help maintain the natural shape of the tissue when suctioned against the supporting surface. In a specific embodiment, where the vacuum arm is non-linear, but has branches 115, the supporting surface on the extended or non-linear portions can be curved or shaped to fit against a nerve. FIG. 4D shows one example of a supporting surface on a linear or elongated vacuum arm having a curvature that can support the shape of a nerve or other similarly-shaped tissue. FIG. 7C shows another example of a supporting surface on a non-linear or extended vacuum arm where the supporting surface of all portions of the vacuum arm are curved to support the shape of a nerve or similarly-shaped tissue.

Figure 11A:
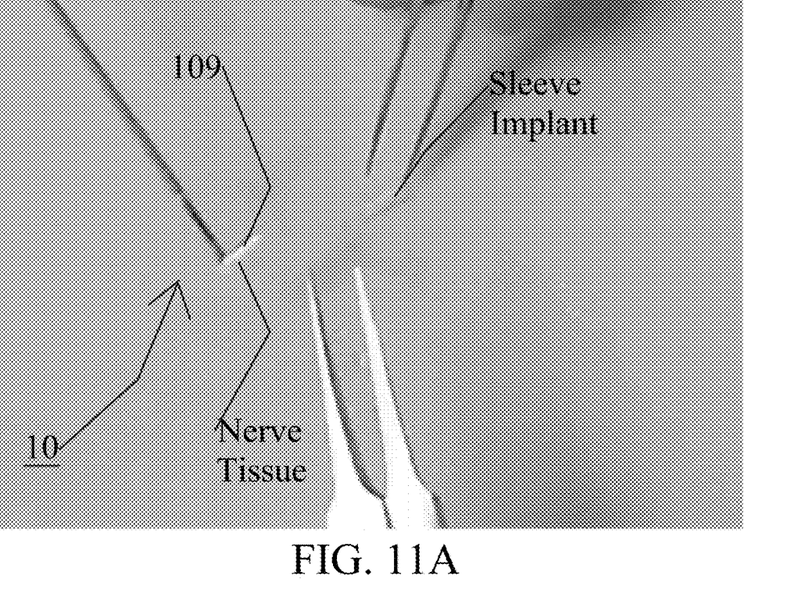
FIGS. 11A and 11B are photographs showing how the supporting surface of a capture-tool, according to the subject invention, can secure a portion of nerve tissue (FIG. 11A) or assist in insertion, or entubulation, of a nerve into a sleeve implant (FIG. 11B).
Figure 11B:
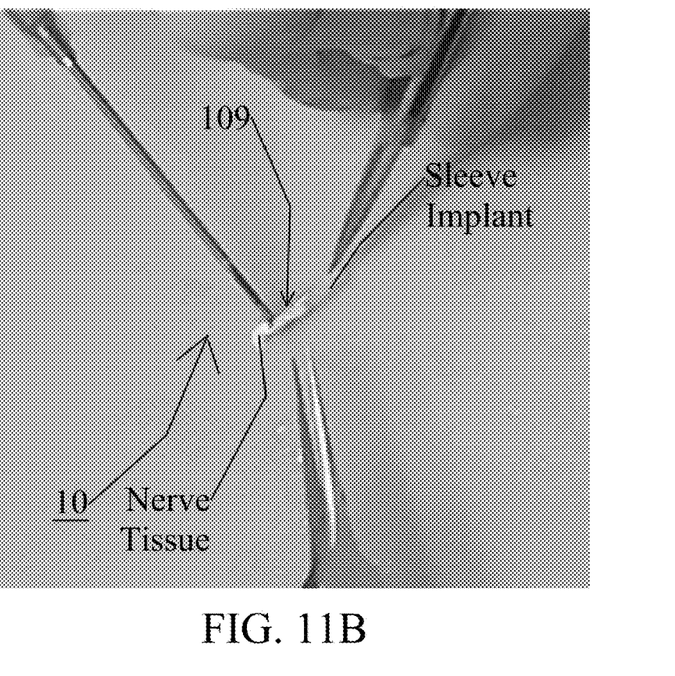

Similarly, it can be advantageous for the viewing surface to be free of protrusions, edges, nibs, scratches, hatching, or other surface features or defects that can inhibit manipulation or entubulation of a tissue. For example, nerves are often repaired using implant sleeves, such as shown, for example, in FIG. 11A, into which the nerves are inserted, as shown in FIG. 11B. The subject invention is particularly suited for holding and manipulating nerve ends into such implants. It can also be advantageous for the viewing surface to have a circumferential form that aids in insertion of the tissue and removal of the vacuum arm from the implant sleeve. In one embodiment, the supporting surface is flat, or substantially flat, providing a generally generic viewing surface for use with a variety of types and sizes of tissues and implants.

In an alternative embodiment, the viewing surface has a curved circumferential form that can be more easily manipulated around other tissues or more easily inserted within other tissues or implants. A person with skill in the art would be able to determine specialized circumferential shapes for a viewing surface that would be useful for specific situations. FIGS. 4B, 4C, and 4D illustrate non-limiting examples of curved viewing surfaces that can be used with embodiments of a vacuum arm of the subject invention.

Tissue can be drawn or pulled up against the supporting surface 110 of a capture-tool 10 by the production of areas or points of low pressure on the supporting surface of the vacuum arm 100. In one embodiment, there are one or more ports 150 within the supporting surface that are in contact with, or connected to, one or more internal conduits 108 in the vacuum arm. As discussed above, a vacuum can be drawn from the one or more internal conduits in the vacuum arm through the channel 55 in the extension. The ports 150 provide openings through which ambient air is drawn through the supporting surface to facilitate the production of vacuum by the formation of targeted low pressure areas on the supporting surface, which is illustrated, for example, by the arrows in FIG. 1. FIG. 12 illustrates a specific embodiment having the supporting surface on the side of the vacuum arm, more adjacent or closer to, rather than opposite to, the viewing surface 109. As such, the ports are directed towards the side of the vacuum arm, as shown in FIG. 12.

The position of the ports within the supporting surface 110 can depend upon several factors, including, but not limited to, the dimensions of the vacuum arm, the type of tissue to be suctioned, the amount of vacuum force obtainable, the number of ports, and other factors understood by those with skill in the art. In one embodiment, there is a port at or near the distal end 4 and a port at or near the proximal end 2 of the vacuum arm. FIG. 1 illustrates an example of this embodiment. In another embodiment, there is a port in the middle of the two ports at either end, which is shown in the example in FIG. 2. In yet another embodiment, there are multiple ports arranged along the length of the supporting surface, an example of which is shown in FIG. 3, where the ellipses indicate the presence of any number of ports.

In one embodiment, the ports are arranged in a single longitudinal row on the supporting surface 110. FIG. 5A illustrates an example of this. In another embodiment, there can be two rows of ports arranged longitudinally on the supporting surface, which is illustrated in FIGS. 5B and 5C. With this embodiment, the ports can be arranged in a staggered, uneven, or alternating fashion, one example of which is shown in FIG. 5B. Alternatively, the ports can be arranged in a side-by-side fashion, as demonstrated in FIG. 5C. There can be other arrangements of the ports within the supporting surface, as would be understood by a person with skill in the art.

Tissue can be suctioned, by the formation of low pressure at the ports, against the supporting surface 110. As such, tissue will be necessarily pulled up against the ports, since the ports are the mechanism by which the tissue is held in place. When the vacuum force is diminished or ceases, the tissue can be automatically freed from against the surface. Vacuum force, as mentioned above, can be adjusted to inhibit the tissue from being drawn too far into the ports, which can inhibit automatic freeing of the tissue. Nonetheless, tissues will be pulled against the edges 152 of the ports. In one embodiment, the edge of a port is beveled, chamfered, filleted, and/or smoothed to reduce the sharpness of the edge. FIGS. 4B and 4C illustrate ports with different types of smoothed edges.

Further, the size and shape of the ports can be configured in a variety of combinations. For example if there are two or more longitudinal rows of ports, they can, but are not necessarily required, to be smaller in diameter than if there was a single longitudinal row of ports. FIG. 5A illustrates a single row of ports with a larger diameter than the ports shown in FIG. 5B, which are arranged in two longitudinal rows. Likewise, the circumferential shape of the ports can be configured in any one or more of numerous options. FIG. 5A shows an example of ports with a circular circumferential shape. FIG. 5B shows an example of ports with an oval circumferential shape. Other non-circular shapes or combinations thereof can also be utilized.

Each port can have a sidewall 155 that defines a duct 157 that connects the internal conduit 108 with the one or more ports 150 on the supporting surface 110. The circumferential shape of the wall can affect the way in which the vacuum pressure travels through the duct to create the low pressure areas at the ports. In one embodiment, the duct has a columnar or substantially constant diameter from the port to the internal conduit. One example of this is shown in FIG. 4D. Alternatively, the duct has a frusto-conical shape, where one end has a smaller diameter than the opposite end. FIG. 4A illustrates one example of a frusto-conical duct that is narrower at the port than where it meets the internal conduit. FIGS. 4B and 4C illustrate examples of frusto-conical ducts that are wider at the port than where they meet the internal conduit. Any of a variety of configurations could be utilized for the wall of a duct.

In some instances, tissue may not be automatically freed or released from the supporting surface 110 when vacuum force is diminished or ceases, that is, when there is no longer low pressure at the ports 150. This can be caused by tissue that may have been pulled into the ports, which can inhibit release. The tissue could also form a vacuum with or become otherwise stuck to the supporting surface, which can also inhibit release. Beneficially, the ports can be used to expel air to assist in releasing tissue from the ports and/or the supporting surface.

As with a vacuum source 6, surgical suites or operating rooms often have an air source for blowing or expelling air, such as for insufflation or clearing away debris. The connector 22 of a capture-tool 10 could be attachable to the same type of air source 10. Alternatively, a separate or different air source could be utilized. In still another alternative, the vacuum and air source can be the same device capable of reversible operation. A person with skill in the art will be able to determine the most appropriate connector and blower source for use with capture-tool embodiments of the subject invention.

In one embodiment, a control mechanism 8 can be used to change or adjust the vacuum force and the expelling of air through the ports 150. Any of a variety of control mechanisms known to those with skill in the art can be utilized and can further be disposed at any location on the capture-tool and/or in-line with the vacuum or air source. FIG. 1 illustrates a non-limiting example of a control mechanism disposed on the handle 20 of a capture-tool.

Utilizing the control mechanism 8, the vacuum force can be adjusted as necessary. Further, the air source can be controlled in both force expelling and the manner of how it is expelled. In one embodiment, the control mechanism can be utilized to expel a quick, short burst or puff of air sufficient to free or release a tissue from the supporting surface and/or the ports. Subsequent short bursts or puffs can be expelled as necessary until the tissue is freed. In another embodiment, the air is expelled with an increasingly stronger force. The force of the stream of expelled air can be adjusted and/or pre-set, so as not to exceed a specific threshold. The control mechanism 8 can be used to expel air as many times as necessary until the tissue is freed or released from the supporting surface. In a still further embodiment, the air is expelled at a constant rate, such that back-pressure at the ports can dislodge the tissue from the supporting surface.

Preferably, the force of the expelled air is not powerful enough to dislodge or displace the tissue from the position in which it was originally placed by the capture-tool. In one embodiment, the force of the expelled air is a fraction of the force utilized to suction the tissue against the support surface. In a further embodiment, the control mechanism allows the force of the expelled air to be under complete manual control, such that a user can determine the method and force by which air is expelled from the ports 150. In an alternative embodiment, the control mechanism is part of a pre-set system, such that a user activates the control mechanism and the system expels air under one or more pre-set conditions. For example, the control mechanism can have multiple settings that control the system so that there can be a neutral or off setting, multiple settings that expel air in specific manners, multiple settings that control vacuum force, and other settings as determined by a person with skill in the art.

When manipulating tissue, it can be difficult to grasp and move tissue without causing damage or undesirable crushing of internal structures. This can be of particular concern with nerves and the manipulations necessary to coapt nerve ends or insert nerve ends into implant devices. The embodiments of the subject invention address these problems by providing a vacuum-assisted capture-tool with ports at which areas of low pressure are formed by the vacuum pressure in the tool. When applied to a tissue, the low pressure at the ports draws the tissue against a supporting surface of the tool and holds it in place. The tissue can then be moved and placed where desired. Once the tissue has been placed, coapted, or otherwise operated on, the vacuum pressure can be turned off to release or free the tissue from the surface. If the tissue is not automatically freed or released, one or more puffs of air can be expelled from the ports to aid in releasing or freeing the tissue.

It should be understood that the examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

The invention claimed is:

1. A method for holding a nerve, the method comprising:
    connecting a capture-tool to a vacuum source, wherein the capture-tool comprises:
        an extension having a proximal end, a distal end, and a channel therethrough that is attachable to the vacuum source,
        a vacuum arm attached to the distal end of the extension and having an internal conduit therein that is continuous with the channel, a viewing surface directed towards the proximal end of the extension and a supporting surface on the exterior of the vacuum arm, and
        one or more ports in the supporting surface connected to the internal conduit;
    adjusting the vacuum source to create low pressure areas at the one or more ports, where the low pressure areas are sufficient to suction the nerve against the supporting surface and minimize the suction of the nerve past the one or more ports;
    placing at least one of the one or more ports against an outer surface of the nerve;
    holding or manipulating the nerve; and,
    releasing the tissue, wherein releasing the nerve comprises one or more of: adjusting the vacuum source to decrease the low pressure areas sufficiently to release the nerve, turning off the vacuum, and expelling positive pressure through the one or more ports.

2. The method according to claim 1, further comprising adjusting the vacuum while the nerve is against the supporting surface to change the vacuum force applied to the nerve.

3. The method according to claim 1, wherein at least a portion of the nerve is held or manipulated for coaptation.

4. The method according to claim 1, wherein the vacuum arm is attached to the extension at an angle of between 30° and 180°.

5. The method according to claim 4, wherein the vacuum arm is attached to the extension at an angle of 90°.

6. The method according to claim 1, wherein the one or more ports comprise two ports with one located at about the proximal end and another located at about the distal end of the vacuum arm.

7. The method according to claim 1, wherein the vacuum arm is linear and the one or more ports are arranged longitudinally on the supporting surface of the vacuum arm.

8. The method according to claim 7, wherein the one or more ports are arranged in at least two rows longitudinally with the vacuum arm.

9. The method according to claim 1, wherein the capture-tool further comprises:
    a branch from the vacuum arm;
    a branch from the vacuum arm with one or more ports on the supporting surface of the branch;
    at least two internal conduits; or
    at least two internal conduits and at least two channels in the extension.

10. A method for placing a nerve in an implant, the method comprising:
    connecting a capture-tool to a vacuum source, wherein the capture-tool comprises:
        an extension having a proximal end, a distal end, and a channel therethrough that is attachable to the vacuum source,
        a vacuum arm attached to the distal end of the extension and having an internal conduit therein that is continuous with the channel, a viewing surface directed towards the proximal end of the extension and a supporting surface on the exterior of the vacuum arm,
        one or more ports in the supporting surface connected to the internal conduit;
    adjusting the vacuum source to create low pressure areas at the one or more ports, where the low pressure areas are sufficient to suction tissue against the supporting surface;
    placing at least one of the one or more ports against an outer surface of a nerve;
    placing at least a portion of the nerve in an implant; and
    releasing the nerve, wherein releasing the nerve comprises one or more of: adjusting the vacuum source to decrease the low pressure areas sufficiently to release the nerve, turning off the vacuum, and expelling positive pressure through the one or more ports.

11. The method according to claim 10, wherein at least a portion of the nerve is held or manipulated for coaptation.

12. The method according to claim 10, wherein the vacuum arm is attached to the extension at an angle of between 30° and 180°.

13. The method according to claim 12, wherein the vacuum arm is attached to the extension at an angle of 90°.

14. The method according to claim 10, wherein the one or more ports comprise two ports with one located at about the proximal end and another located at about the distal end of the vacuum arm.

15. The method according to claim 10, wherein the vacuum arm is linear and the one or more ports are arranged longitudinally on the supporting surface of the vacuum arm.

16. The method according to claim 15, wherein the one or more ports are arranged in at least two rows longitudinally with the vacuum arm.

17. The method according to claim 10, wherein the capture-tool further comprises a branch from the vacuum arm.

18. The method according to claim 17, wherein the capture-tool further comprises one or more ports on the supporting surface of the branch.

19. The method according to claim 10, wherein the capture-tool further comprises at least two internal conduits.

20. The method according to claim 19, wherein the capture-tool further comprises two channels in the extension.

* * * * *